US012663410B2

(12) United States Patent
Stangeland

(10) Patent No.: US 12,663,410 B2
(45) Date of Patent: Jun. 23, 2026

(54) TESTING FIBER LOSS IN FABRICS

(71) Applicant: Under Armour, Inc., Baltimore, MD (US)

(72) Inventor: Jeremy Stangeland, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 284 days.

(21) Appl. No.: 18/340,405

(22) Filed: Jun. 23, 2023

(65) Prior Publication Data

US 2023/0417729 A1 Dec. 28, 2023

Related U.S. Application Data

(60) Provisional application No. 63/355,202, filed on Jun. 24, 2022.

(51) Int. Cl.
| | |
|---|---|
| *G01N 33/36* | (2006.01) |
| *G01N 1/14* | (2006.01) |
| *G01N 1/28* | (2006.01) |

(52) U.S. Cl.
CPC ............. *G01N 33/367* (2013.01); *G01N 1/14* (2013.01); *G01N 1/286* (2013.01); *G01N 2001/2873* (2013.01)

(58) Field of Classification Search
None
See application file for complete search history.

(56) References Cited

FOREIGN PATENT DOCUMENTS

| | | | |
|---|---|---|---|
| CN | 203570560 U | * | 4/2014 |
| CN | 111103231 A | | 5/2020 |
| WO | 2021039520 A1 | | 3/2021 |

OTHER PUBLICATIONS

De Falco, F. et al., "Quantification of Microfibres Released During Washing of Synthetic Clothes in Real Conditions and at Lab Scale", The European Physical Journal Plus, vol. 133, No. 257, 2018, pp. 1-4.*
Pirc, U. et al. "Emissions of Microplastic Fibers from Microfiber Fleece During Domestic Washing", Environ Sci Pollut Res, vol. 23, Sep. 22, 2016, pp. 22206-22211.*
De Falco, F. et al., "Evaluation of Microplastic Release Caused by Textile Washing Processes of Synthetic Fabrics", Environmental Pollution, vol. 236, 2018, pp. 916-925.*

(Continued)

*Primary Examiner* — Daniel S Larkin
(74) *Attorney, Agent, or Firm* — Edell, Shapiro & Finnan, LLC

(57) ABSTRACT
A method of determining an amount of fiber loss or fiber shedding from a fabric material after washing of the fabric material includes providing a sample of the fabric material within a container, adding water into the container to facilitate contact of the water with a surface of the sample, agitating the water within the container for a predetermined period of time so as to cause fibers to be released from the fabric material and entrained in the water, after agitating, transferring the water with entrained fibers from the container into a fiber collection system to obtain captured fibers, and analyzing the captured fibers to determine a degree of fibers shed from the fabric material. A method of determining a quality of fiber material based upon fiber shedding from the material is also described.

18 Claims, 8 Drawing Sheets

(56) References Cited

OTHER PUBLICATIONS

Napper, I. et al., "Releases of Synthetic Microplastic Plastic Fibres from Domestic Washing Machines: Effects of Fabric type and Washing Conditions", vol. 112, 2016, pp. 39-45.*

Kelly, M. et al., "Importance of Water-Volume on the Release of Microplastic Fibers from Laundry", Environmental Science and Technology, vol. 53, 2019, pp. 11735-11744.*

International Search Report and Written Opinion in counterpart International Application No. PCT/US2023/068972, mailed Oct. 10, 2023, 13 pages.

Tiffin et al., "Reliable quantification of microplastic release from the domestic laundry of textile fabrics," The Journal of the Textile Institute, 2022, 113:4, pp. 558-566, DOI: 10.1080/00405000.2021.1892305.

Carney Almroth et al., "Quantifying shedding of synthetic fibers from textiles; a source of microplastics released into the environment," Environmental Science and pollution research 25 (2018): pp. 1191-1199, DOI: 10.1007/s11356-017-0528-7.

Extended European Search Report in counterpart European Application No. 23828080.4-1001, mailed May 7, 2026, 14 pages.

* cited by examiner

CONNECT SYSTEM COMPONENTS, INCLUDING FUNNEL WITH FLASK AND FILTER DISPOSED THEREBETWEEN — 310

POUR CONTENTS OF CONTAINER INCLUDING ENTRAINED FIBERS INTO FUNNEL — 320

APPLY VACUUM TO FLASK FOR DESIRED TIME PERIOD — 330

REMOVE FILTER FROM BETWEEN FUNNEL AND FLASK AND PREPARE FILTER FOR ANALYSIS — 410

ANALYZE FILTER UNDER MAGNIFIED VIEW — 420

ASSIGN FIBER LOSS/FIBER SHEDDING VALUE TO SAMPLE BASED UPON ANALYSIS — 430

USE FIBER LOSS/SHEDDING VALUE TO DETERMINE QUALITY/USE OF FABRIC — 440

TESTING FIBER LOSS IN FABRICS

CROSS-REFERENCE TO RELATED APPLICATION

This application claims priority from U.S. Provisional Patent Application Ser. No. 63/355,202, filed Jun. 24, 2022, the disclosure of which is incorporated herein by reference in its entirety.

FIELD OF THE INVENTION

The present invention relates to a method of testing loss of fibers in a fabric, such as a fabric for use in apparel products.

BACKGROUND

Fibers used to form fabrics have been getting increasingly smaller in dimensions to enhance properties of the fabrics, such as softness and durability of the fabrics. In particular, ultra-fine or microfibers, which comprise synthetic fibers having cross-sectional dimensions/diameters no greater than 10 micrometers and short lengths (e.g., 5 millimeters or less) can be formed from polyester, polyolefins of any other suitable types of polymers and combinations thereof, and such micro-fibers can be combined to form fabrics having desired softness, deniers, tensile strength and/or other properties suitable for a particular textile implementation.

While the use of microfibers provides a variety of enhanced and desirable properties in the formation of fabrics, such microfibers can also present problems when released or shed from garments or other fabrics, particularly when washed. In a typical laundry wash cycle, a garment formed from microfibers can release or shed on average about 700,000 microfibers into waste water. The microfibers can be difficult to remove from the waste water and can wind up in lakes, streams and oceans. Further, the microfibers can absorb toxins when present in waterways and can further be detrimental to ecosystem with such waterways.

In addition, fabrics including fibers other than ultra-fine or microfibers can also suffer from fiber loss/fiber shedding when worn and/or when washed in a laundry wash cycle.

It would be desirable to provide an easy, relatively quick and accurate process for determining a rate or amount of fiber loss or fiber shedding in a fabric for different types of fabrics when the fabrics are washed (e.g., in a laundry wash cycle). This in turn would facilitate shifting away from certain types of fabrics that are determined to shed fibers to a greater extent in comparison to other types of fabrics.

SUMMARY OF THE INVENTION

In example embodiments, a method is provided of determining an amount of fiber loss from a fabric material after washing of the fabric material. The method can comprise providing a sample of the fabric material within a container, the sample having a shape defined by peripheral edge portions of the sample, adding water into the container to facilitate contact of the water with a surface of the sample that faces the water while preventing the water from contacting the peripheral edge portions of the sample, and agitating the water within the container for a predetermined period of time so as to cause fibers to be released from the fabric material and entrained in the water. After agitating, the water with entrained fibers can be transferred from the container into a fiber collection system to obtain captured fibers, and the captured fibers can be analyzed to determine a degree of fibers shed from the fabric material.

In other example embodiments, a method of determining a quality of a fabric material comprises determining a degree of fiber shedding associated with a fabric material, and assigning a quality grade for the fabric material based upon the determined degree of fiber shedding.

In further example embodiments, a method comprises determining an amount of fiber loss from a fabric material after washing of the fabric material. The method comprises obtaining a sample of the fabric material, providing the sample within a container member such that edges of the sample are pinched and covered by two facing surfaces of the container member, adding water into the container member, where adding water into the container facilitates contact of the water with a surface of the sample that faces the water, and agitating the water within the container member for a predetermined period of time so as to cause fibers to be released from the fabric material and entrained in the water. After the agitation, the water with entrained fibers is poured or transferred from the container member into a fiber collection system comprising a vessel of a filtration system, where the filtration system includes a filter in fluid communication with the vessel. The method further comprises facilitating removal of the water from the vessel by passage of the water through the filter while fibers entrained in the water are collected on the filter, analyzing the fibers collected on the filter, and assigning an indicator of fiber loss to the fabric material based upon the analyzing the fibers collected on the filter.

The sample can be obtained by cutting the sample from the fabric material.

In addition, the container member can comprise a container with a lid that is securable to an open end of the container, and the sample is provided between the container and the lid and the lid is secured to the container such that the edges of the sample are pinched and covered by the facing surfaces of a container edge at the open end of the container and a surface of the lid that faces the container edge.

The above and still further features and advantages of the present invention will become apparent upon consideration of the following detailed description of specific embodiments thereof.

Figure 1:
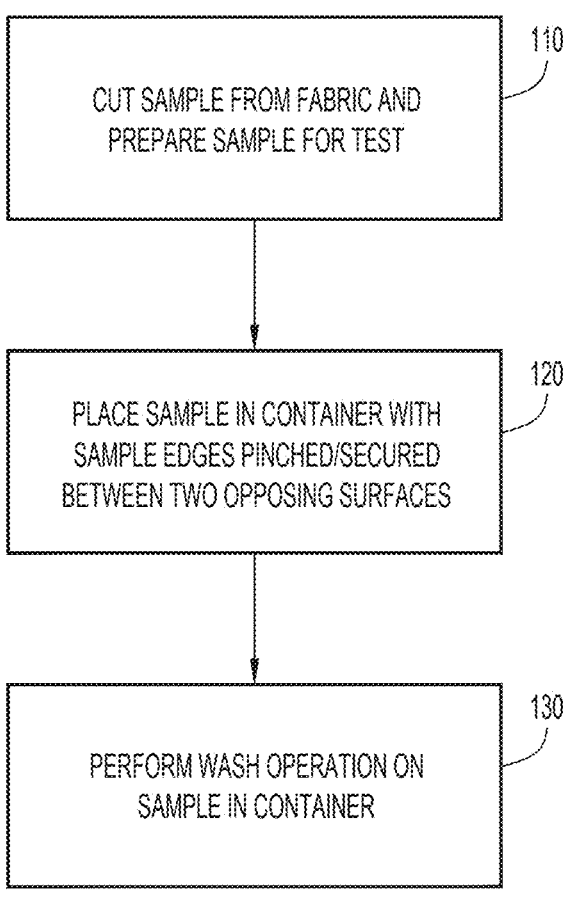
FIG. 1 is a flowchart depicting method steps associated with a first operational phase of the fiber loss/fiber shedding test methods described herein.

Like reference numerals have been used to identify like elements throughout this disclosure.

DETAILED DESCRIPTION

In the following detailed description, reference is made to the accompanying figures which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Methods are described herein that facilitate testing of fabrics to find yarns or combinations of yarns in fabrics that don't lose or shed fibers or that lose or shed a much lower number/amount of fibers in comparison to other types of fabrics. In particular, the methods described herein facilitate the discovery of yarns or combinations of different yarns that can be used to form fabrics that significantly minimize or prevent shedding of fibers when the fabrics are washed, which in turn prevents or minimizes accumulation of fibers released from fabrics into waterways and ecosystems.

In example embodiments, a method for testing a fabric for fiber loss or fiber shedding characteristics can comprise removing a test sample from a portion or a swatch of the fabric, e.g., by cutting the sample so as to have a specific shape and dimension(s) from the fabric. The edges of the sample are highly susceptible to release or shedding of fibers, due to ends of fibers being free at the cut edges (i.e., not interlocked with other fibers along the fabric sample). To prevent fibers at the edges from freely separating or shedding during the process (which would likely lead to inaccurate test results that would exaggerate the fiber shedding values), the peripheral edge portions of the test sample are covered to prevent any fibers from the edges from being captured with fibers shedding from other portions of the sample during testing. For example, the peripheral edge portions of the sample can be wedged between two surfaces as described herein so as to be inaccessible (not exposed) to a washing cycle of the test process that determines an amount or degree of fiber shedding. In other words, water is prevented from contacting the peripheral edge portions of the fabric sample.

The test sample is then subjected to a washing procedure (in which a portion of the sample is submerged in water) that simulates a typical laundry wash cycle, followed by washing or rinsing of the test sample and collecting liquid used to rinse the test sample. The collected liquid is then processed in a fiber collection system to determine a degree to which fibers are shed or removed from the fabric material as a result of the washing process. For example, the collected liquid can be filtered using a process as described herein, and fibers separated from the liquid are collected on the filter. The filter including fibers collected thereon is analyzed to determine a quantity of fibers present on the filter, and this quantity is correlated with a number or amount of fibers that have been released or shed from the sample and thus the quality of the fabric with regard to fiber retention. The fiber shed quantity or amount that is determined can be utilized to assess a quality of a particular fabric prior to deciding whether to implement such fabric for manufacturing a particular textile product, such as an article of apparel.

The fiber loss or fiber shedding test methods described herein can be utilized for any type of fabric that is formed with any one or more types of fibers including, without limitation, fabrics that are formed via any type of knitting process (e.g., to form a knit fabric), weaving process (e.g., to form a woven fabric), embroidering process (e.g., to form an embroidered fabric), a nonwoven process (e.g., to form a nonwoven fabric) or any combinations thereof.

The fibers used to form fabrics subjected to the fiber shedding test as described herein can be formed as continuous filaments (i.e. synthetic fibers of continuous/infinite lengths that are typically wound together to form the fabric) and/or staple fibers (i.e., fibers of short lengths twisted together to form one or more yarns), where the fibers can be formed as any suitable types of yarns having any suitable sizes, suitable deniers and further where the fibers can have cross-sectional dimensions or diameters and/or lengths of any suitable sizes including ultra-fine or micro fibers (e.g., fibers having cross-sectional dimensions in the micrometer range no greater than 10 microns and lengths no greater than 5 microns) or even fibers that are larger (not ultra-fine or micro fiber sizes).

Further, the fibers can be natural (e.g., wool, silk, cotton, bamboo, soybean, etc.) or synthetic, where synthetic fibers can be formed of any one or more suitable types of polymers including, without limitation, polyolefins (e.g., polyethylene, polypropylene, etc.), polyurethanes, polyesters (e.g., polyethylene terephthalate), polycaprolactam, poly(hexamethylene adipamide), acrylic, acetate, rayon, polyamide (nylon), aramid (e.g., Kevlar) and any selected combinations thereof. Furthermore, the fibers can be chosen to form fabrics for fiber shedding tests that have any suitable degree of elasticity, e.g., fabrics formed from elastane fibers comprising an elastomeric polyester-polyurethane copolymer (e.g., Spandex).

Ultra-fine or microfibers can be problematic for certain types of fabrics in that these fibers can be more susceptible to shedding in wash cycles for the fabric. In addition, certain types of abrasion processing of continuous fibers (e.g., brushing, sueding, napping, etc.) to make the fabric have a softer feel can also result in an increase in shedding of such fibers from the fabric. The testing methods described herein, which provide an accurate indication of an amount or degree of fiber shedding within the fabric, can facilitate the formation of fabrics (e.g., based upon fiber and/or fabric forming techniques, types of fibers and/or yarns used to form the fabrics, etc.) that will have a lower level of fiber shedding.

An example method for testing fiber shedding of a fabric is described with reference to the figures. A first operational phase of the method is described in the flowchart depicted in FIG. 1 and the example embodiment of a container or vessel 140 that receives a sample 145 and a stir bar 150 and further secures to a lid 160. At 110, a sample (e.g., sample 145) is cut from a fabric that is selected for testing, and the sample can be further prepared for testing. The fabric can be from a swatch of fabric considered for use or used in forming a particular article of apparel or other textile product. A cutting die or cutter can be used to cut the sample from the fabric having suitable dimensions for use in the test. The sample can be cut or removed from the fabric having any desired geometric shape (e.g., circular, polygonal, such as triangular, rectangular, etc., or irregular shaped). In an example embodiment, the sample can be cut into a shape that generally corresponds with a cross-sectional shape of the container within which the sample is washed. In a further example embodiment, the cutter cuts or removes a sample from the fabric to be tested having a circular shape with a diameter of a specified dimension (e.g., cut with a diameter ranging from about 50 mm to about 80 mm, or from about 60 mm to about 70 mm, such as a diameter of 68.53 mm) to fit within a container (e.g., vessel 140) as described herein. After the sample is cut, it can be prepared for testing by vacuuming the sample for a select number of times and a selected duration to ensure any loose fibers associated with the sample due to the cutting/removal from the fabric are removed and not part of the test. For example, a shop vacuum or any other suitable vacuum source can be used to apply suction to one or both sides of the sample (e.g., while holding an edge of the sample). In a specific, non-limiting example, the sample can be held at its edge and inserting the sample within a vacuum tube for about two seconds, followed by rotation by 90° of the sample and then reinsertion into the vacuum tube for another two seconds. The sample can be stored, e.g., within a covered petri dish or other enclosure prior to the sample being subjected to the next step of the process.

At 120, the sample removed from the fabric is placed in a container such that the peripheral edges of the sample are covered and not exposed during the fiber testing in which the sample is treated with water (as described herein). In an example embodiment, the peripheral edge portions of the sample are pinched and secured between two, facing surfaces of the container such that the sample edges are not exposed to an interior volume defined by the container.

Figure 1A:
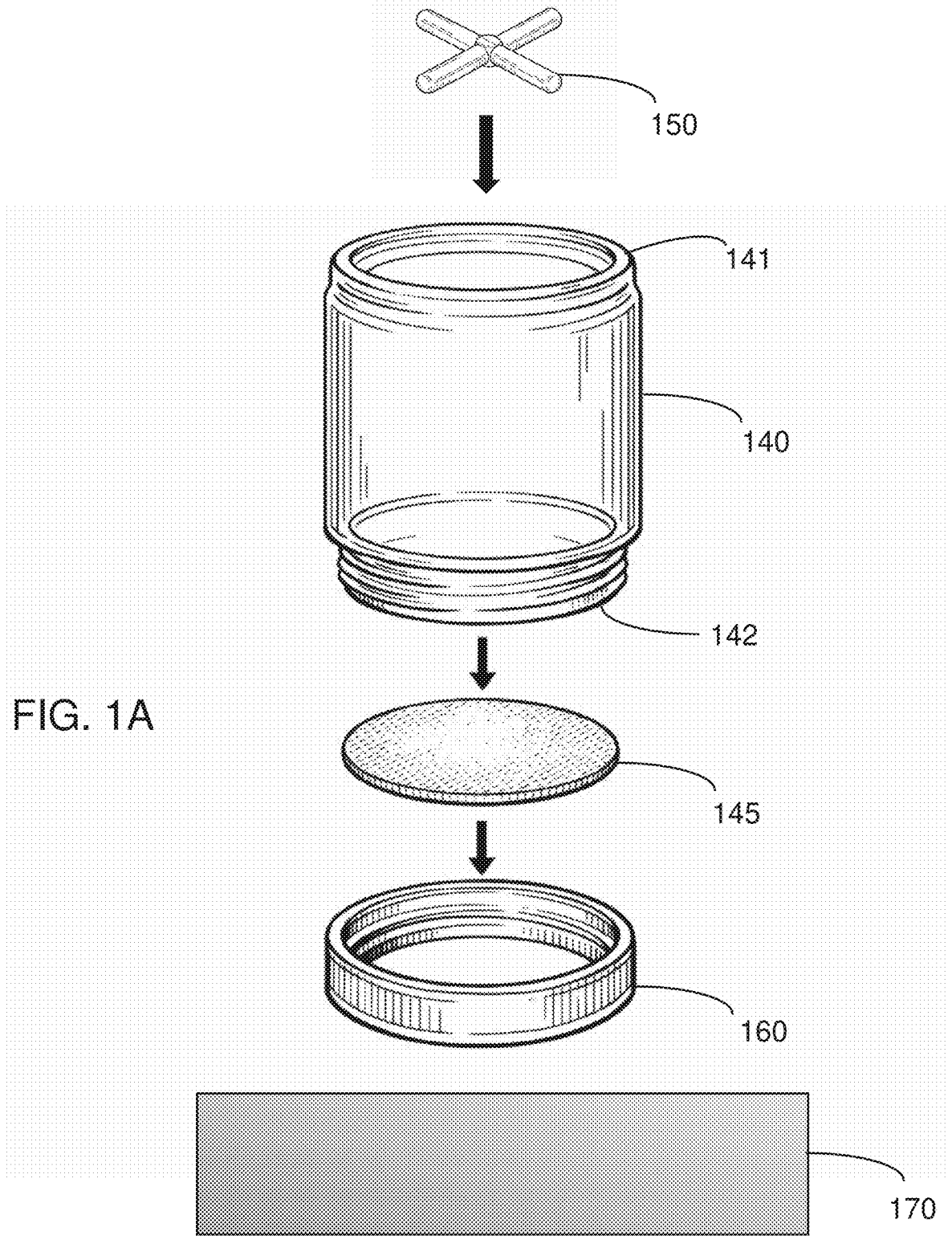
FIG. 1A is a schematic illustration of an example embodiment of a container with sample, lid, stir bar and stir plate used for the washing operation described herein and shown in the flowchart of FIG. 1.

Referring to FIG. 1A, the container can comprise, e.g., a jar or vessel 140 formed of glass or other suitable material that includes a first open end 141 and a second open end 142 that is configured to be closed in a fluid tight seal with an enclosure or lid 160. For example, the container can comprise an open bottom Mason jar or similar vessel 140 in which the first end 141 is open (i.e., no bottom or enclosed surface), and the second open end 142 is threaded and configured to receive a lid 160 that screws (or attaches in any other manner) to the second open end 142 so as to provide an adequate liquid seal at the second open end. To achieve a desired fluid tight seal, PTFE (polytetrafluorethylene) tape or other suitable sealing material can be wrapped around the threaded second open end 142 of the jar or vessel 140 prior to securing the lid 160 to the jar. The sample 145 can be cut with suitable dimensions so as to correspond with and fit snug at a closed end within the inside of the lid 160 such that, when the lid 160 is connected with the second open end 142 of the jar 140, the entire periphery or edges of the sample 145 are pinched and secured between the lid 160 and the second open end 142 of the jar 140 (i.e., pinched between two facing surfaces of the container, the surface of the lid and the surface or edge portions of the open end of the jar). For example, the sample can be handled with tweezers and placed within the lid, with the lid then being secured to the jar. This securing of the sample between lid and jar minimizes any foreign fibers or other substances from adhering to the sample prior to being secured within the jar and also effectively covers the sample edges so as to not be exposed to or accessible within the internal volume of the jar.

The first end 141 of the jar 140 is open to facilitate filling of the jar with a selected or predetermined amount of water. At 130, a wash operation is performed on the sample at ambient or room temperature (e.g., from about 20° C. to about 28° C.). In particular, a magnetic stir bar 150 (e.g., a 40 mm cross shaped magnetic stir bar) is placed within the jar 140 so as to rest over the sample 145 and lid 160 at or near the second end 142 of the jar. Alternatively, the magnetic stir bar can first be placed over the sample disposed within the lid, and then the lid secured with the second open end of the jar with both sample and magnetic stir bar located on the lid. After securing of the lid with the jar and both sample and magnetic stir bar being within the internal volume of the jar at the open second end (and supported by the lid), a desired or predetermined amount of water is then added within the internal volume of the jar via the first open end of the jar so as to completely submerge the sample and stir bar in water within the jar. For example, 200 mL of type II water (e.g., distilled and/or deionized water) can be poured into the jar at the first open end. Once the water is placed within the jar, a petri dish or other enclosure can be placed over the first open end of the jar. This encloses the sample and water within the jar and prevents unwanted dust and/or other airborne particles from entering the jar.

The jar 140 is then placed on a stir plate 170. The stir plate 170 includes a component that induces a magnetic field to cause the magnetic stir bar within the jar to spin at a desired rotational velocity or stir rate. For example, the stir rate of the stir plate can be set for a rotation of the stir bar to about 300 RPM (e.g., 310 RPM). The stirring of the water by the stir bar can be implemented for a sufficient period of time (e.g., about 3-7 minutes, such as about 5 minutes) at ambient or room temperature so as to simulate agitation of water against the sample that corresponds with the fabric being subjected to a typical laundry wash cycle. After performing the simulated wash cycle, the jar with enclosure (e.g., petri lid) covering the first open end is allowed to rest until the next or second operational phase of the test method as described herein.

In an alternative embodiment of the first operational phase, stirring of the water within the jar that includes the sample can be achieved using a stir bar having any suitable shape (e.g., cross-shape, linear shape, etc.) and a rotational rod attached to the stir bar and which extends from the jar and connects with a rotational motor. The rotational motor spins the rod and stir bar at a suitable rotational speed (e.g., about 300 RPM). Instead of using a cover (e.g., a petri dish) over the first end of the jar, one or more covers or plates can instead be used which are effective to enclose or seal the contents within the jar (thus preventing dust or other air-borne particles from entering the jar) while allowing rotation of the rod and stir bar by the motor located exterior to the jar. For example, a pair of plates can be provided, each plate having sufficient dimension(s) to cover the opening at the first end of the jar and further including a generally linear slot that extends from a peripheral side or edge of the plate to a central region of the plate. Each linear slot further has a width that is sufficient to permit the rotational rod to extend through the slot and to rotate while extended through the slot. A first plate of the pair can be placed onto the first end of the jar with its slot arranged in a first direction, while the second plate of the pair is then placed over the first plate with its slot arranged in a second direction that is offset from the first direction (e.g., rotated by 90° in relation to the first direction). This effectively provides an opening for insertion of the rotational rod through the first and second slots of the plates while minimizing exposure of the internal contents of the jar from the slots, since communication between a significant or major portion each slot with the jar interior is effectively prevented by the first or second plate (i.e., each of the first and second plates provides a cover for the jar interior over a majority of the length of the slot for the other of the first and second plates). In addition, the stir bar can be placed at any selected distance from the sample within the jar (e.g., resting against sample, or spaced a selected distance from the sample). In operation, a portion of the rod and the stir bar can be inserted within the interior of the jar, followed by placement of the first and second plates in the previously described orientations around the portion of the rod extending from the jar interior at the first open end to provide an enclosure for the jar while permitting rotation of rod and stir bar within the jar.

Figure 2:
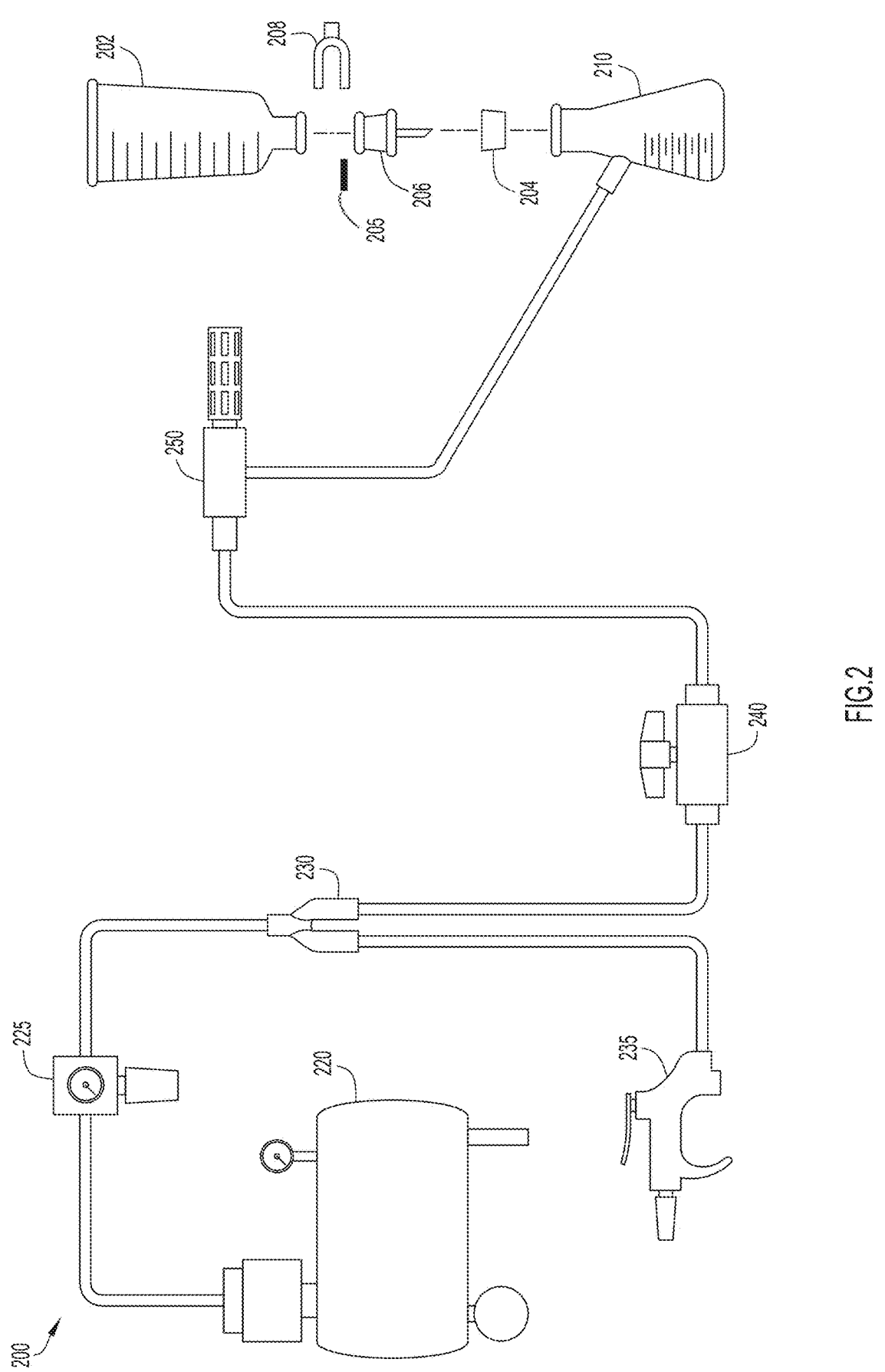
FIG. 2 is a schematic illustration of an example embodiment of a filtration system used for a second operational phase of the fiber loss/fiber shedding methods described herein.
Figure 3:
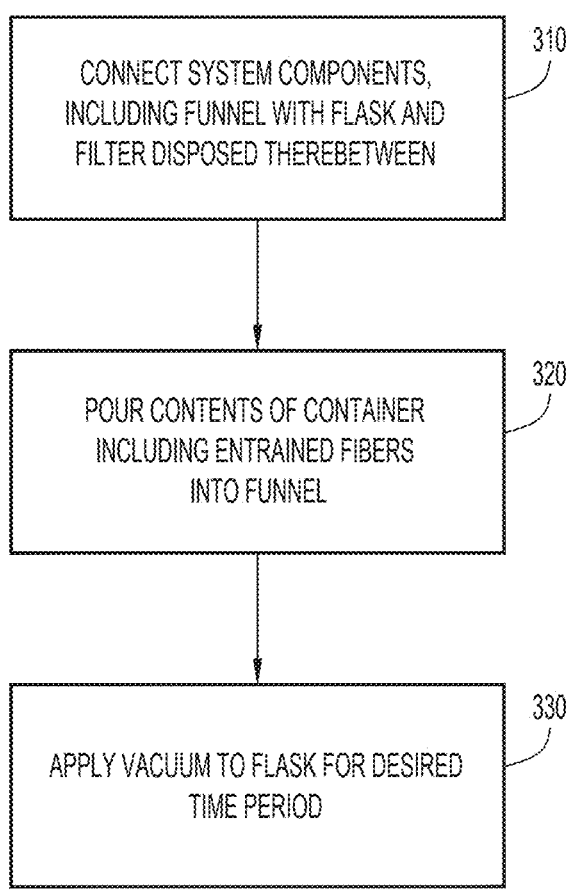
FIG. 3 is a flowchart depicting method steps associated with the second operational phase of the fiber loss/fiber shedding test methods described herein and utilizing a filtration system such as that depicted in FIG. 2.

The next or second operational phase of the fiber loss/fiber shedding test method is now described with reference to the schematic diagram of FIG. 2 and the flowchart of FIG. 3. An example vacuum filtration system 200 is depicted is FIG. 2, where the system 200 captures fibers shed from the sample and entrained in the water of the container that results from the agitation/simulated wash cycle of the first operational phase. As described herein, the system 200 facilitates capturing of fibers shed from the fabric (during the wash cycle/first operational phase) and entrained within the water on a filter of the system 200.

The system 200 includes a funneling kit including a filtration funnel 202 including an open upper end and an open lower end (where the funnel at least partially tapers in cross-sectional dimension from its wider open upper end to its narrower or smaller open lower end), a stopper 204 (e.g., formed of a rubber and/or other resilient material), and a tube 206 including a seat that secures (e.g., with a clamp 208) in a fluid and airtight sealed relationship to a lower open end of the funnel 202. The stopper includes a passage that extends through the stopper, and the tube is fit within at least a portion of the stopper passage so as to facilitate a flow of water or other fluid through the stopper via the passage and tube. The filtration funnel 202 can include graduated markings (e.g., in mL) to facilitate easy delivery of a specific amount of fluid into the funnel. The stopper 204 fits snugly as an air and fluid tight bung within an opening of a filtration vessel or filtering flask 210. Both the funnel 202 and the flask 210 are suitably dimensioned to hold and process a sufficient amount of water (e.g., 300 mL or greater) during the filtration process. Thus, the connections as shown in FIG. 2 facilitate a flow of water from the funnel 202, into and through the tube 206 (including the seat), through the stopper 204 (e.g., via the tube 206 and/or the passage of the stopper 204), and into the flask 210.

A filter 205 is secured between the seat of the tube 206 and the lower end of the funnel 202 (i.e., at the location at which the clamp 208 secures both components together). In particular, the seat of the tube 206 can include, at an upper end (or end that engages or is securable with the lower open end of the funnel 202), a depression or indentation that is suitably dimensioned to receive and retain the filter 205. In example embodiments, the filter is hydrophilic to enhance the flow of water through the filter and separation of fibers and/or other solid material from the water. The filter 205 has suitable dimensions (e.g., a dimension/diameter ranging from about 20 mm to about 30 mm, e.g., a dimension/diameter of about 25 mm) to ensure an adequate fit at the seat of the tube 206 and a suitable porosity to permit water to freely flow through the filter while preventing shed fibers from the fabric sample and entrained in the water from passing therethrough. For example, the filter can have a suitable porosity or pore size (i.e., to facilitate retention/capture of particles having dimensions of at least such pore size) of at least 0.5 microns (micrometers), or of at least 0.6 microns, or of at least 0.7 microns, or of at least 0.8 microns. Such filter pore sizes can effectively collect micro-sized fibers having cross-sectional dimensions or diameters in the range of 10 micron or less, or even 5 micron or less, or further 1 micron or less. A particularly suitable type of filter material that has been determined highly effective in the fiber shedding test methods described herein comprises a mixed cellulose ester (MCE) membrane filter material. A MCE membrane filter material comprises a pure, biologically inert mixture of cellulose acetate and cellulose nitrate. In an example embodiment, the MCE filter can be used having a 5.0 micron pore size, 25 mm diameter and commercially available from Tisch Scientific (Ohio, US).

The flask 210 includes an outlet port extending transversely from a side and being near but separate from the open upper end of the flask. The outlet portion is suitably dimensioned to facilitate coupling or connection of the flask 210 in an air tight manner, via its outlet port and suitable compressed air tubing, to a suitable vacuum source. In the system 200, the vacuum source generates a vacuum or negative pressure at the air outlet from the flask 210 via a combination of components including an air compressor 220, a pressure regulator 225, an air line splitter 230, an air gun 235, and a shut-off valve 240, a Venturi vacuum device 250, and flexible compressed air tubing providing connections between the components and the flask 210.

The air compressor 220 generates a flow of compressed air that is delivered (via tubing) to the pressure regulator 225, where the pressure regulator 225 regulates the air pressure to a desired value (e.g., about 60 psi or about 0.41 MPa). The pressurized air is delivered from the regulator 225 (via tubing) to the air line splitter 230 which splits the air stream (via tubing) to the air gun 235 and the shut-off valve 240. Compressed air from shut-off valve 240 is delivered (via tubing) to the Venturi vacuum device 250. The Venturi vacuum device 250 is configured in a conventional manner (i.e., via a nozzle that restricts air flow within the device) to draw a vacuum from a first port while the compressed air flows through a second port. The first port of the Venturi vacuum device 250 is connected (via tubing) to the outlet port of the flask 210.

The process steps of the second operational phase, utilizing system 200, is described with reference to the flowchart of FIG. 3. At 310, the equipment/components of the system 200 are connected together in the previously described manner. In the connection of the funnel 202 with the flask 210, the seat of the tube 206, which includes a sintered filter holder, can first be slightly wetted with a few drops of deionized water before inserting the filter on the seat. This can enhance the fitting of the filter onto the seat. The filter can be handled with tweezers and placed onto the seat of the tube 206, and the tube 206 and funnel 202 are connected together (e.g., with clamp 208). The tube 206 is also inserted through the stopper 204 and the stopper is fit at the open upper end of the flask 210. An enclosure (e.g., a petri dish) can be placed over the open top end of the funnel 202 to prevent any airborne and/or other particulate matter from entering the funnel prior to addition of water into the funnel.

A tweezers can be used to remove the magnetic stir bar from the container (e.g., jar) including water (which includes entrained fibers shed from the fabric sample) and the fabric sample from the first operational phase. The magnetic stir bar can be completely rinsed with deionized water that then flows into the container, where this rinsing can effectively capture any shed fibers entrained in the water that may have adhered to the stir bar during its removal. At 320, the water including entrained fibers is then poured into the funnel 202. The container is rinsed a desired number of times with deionized water, where the rinsing can be performed, e.g., with a squeeze bottle including a nozzle to control and selectively direct water flow into the container and where the rinsing includes washing the side walls of the container. For example, the container can be rinsed a single time or any desired number of times (e.g., 2-4 times) with deionized water, where the water is then poured into the funnel 202. The container can be rinsed with deionized water and the water poured into the funnel 202 until the total volume within the funnel is about 300 mL. Without any vacuum applied to the funnel 202 and flask 210, the water is substantially retained in the funnel 202.

At 330, vacuum is applied to the funnel 202 and flask 210 in the following manner. Compressed air generated by the air compressor 220 is regulated by regulator 225 (e.g., to a pressure of about 60 psi or about 0.41 MPa) and delivered to the air line splitter 230, which further delivers the compressed air to air gun 235 and shut-off valve 240. In the vacuum application mode, air gun 235 is closed while the shut-off valve 240 is open and allows the compressed air to flow to the Venturi vacuum device 250. The Venturi vacuum device 250 generates a vacuum in the flask 210, which causes water including entrained fibers to be forced downward toward the filter, where the water passes through the filter and seat of the tube 206 and into the flask 210. Fibers entrained in the water are prevented from passing through the filter but instead collect on the filter while the water passes through the filter. The amount of water in the funnel 202 can be monitored. Once the volume of water in the funnel 202 is at a certain amount (e.g., about 100 mL), the walls of the funnel can be washed with deionized water (e.g., using the squeeze bottle) so as to ensure that any fibers from the water that might adhere to the sidewalls of the funnel are washed downward and are captured by the filter. When all the water from the funnel 202 has been drawn through the filter and into the flask 210, the vacuum applied can be continued for a desired period of time (e.g., about 10 seconds, or about 30 seconds, or about 1 minute or longer) so as to ensure any water entrained in the filter continues to flow from the filter. After sufficient vacuum has been applied, the vacuum can be ceased at the flask 210 by closing the shut-off valve 240, opening the air gun 235 and turning off the air compressor 220 (in any selected order).

The second operational phase effectively separates fibers shed from the fabric sample from the water within which the fibers were entrained in the first operational phase. The separated fibers are collected on the filter, and the filter is then examined in a further, third operational phase to determine an amount or degree of fiber loss/fiber shedding associated with the fabric. Prior to analyzing the filter including captured fibers, the open top of the funnel 202 can be covered (e.g., using a petri dish) so as to prevent any airborne particulates from falling into and contaminating the filter to be analyzed.

Figure 4:
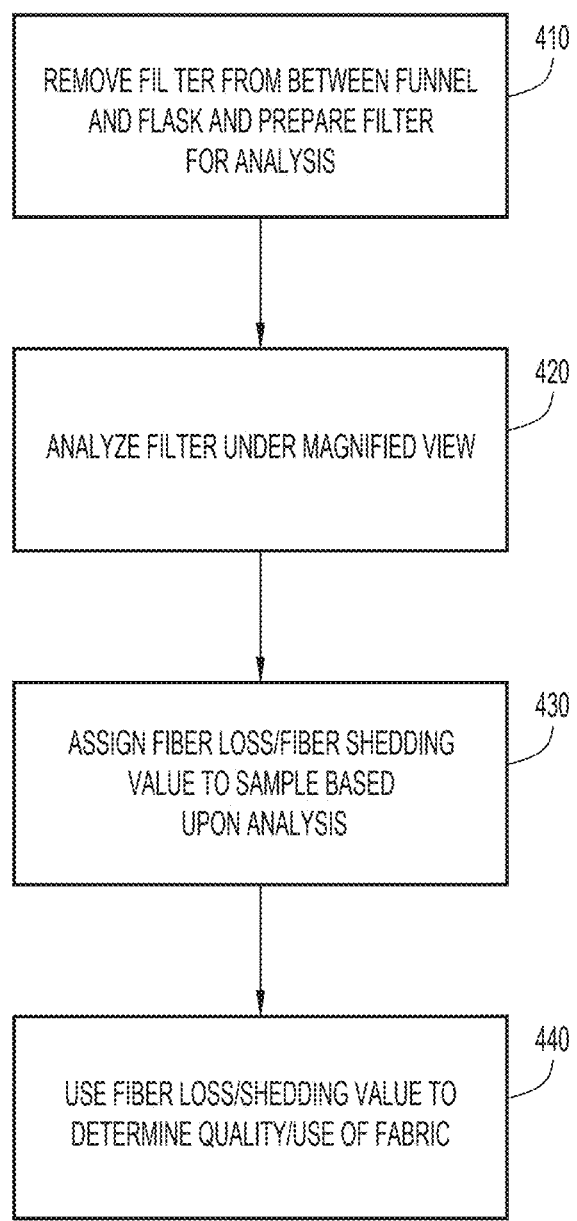
FIG. 4 is a flowchart depicting method steps associated with a third operational phase of the fiber loss/fiber shedding test methods described herein.

The third operational phase of the fiber loss/fiber shedding test method is now described with reference to the flowchart of FIG. 4 and the images set forth in FIGS. 5A-5E. At 410, the funnel 202 is separated from the flask 210 by disconnecting the tube 206 from the funnel 202 and carefully removing the filter (e.g., using tweezers) and preparing the filter for analysis. A pair of transparent (e.g., glass) microscope slides are suitably cleaned (e.g., with lens wipes). A pair of double-sided tape strips can be applied to one of the slides, and the filter carefully placed (e.g., using tweezers) upon that slide and between the tape strips. The other slide can then be placed over the slide that includes the filter so that the filter is located between the two slides and the slides are secured together via the double-sided tape strips.

At 420, the slide configuration including the filter is examined in a magnified view (with filter side including the captured fibers being up or toward the magnifying lens) so as to determine an amount or degree of fibers captured by the filter. In example embodiments, a microscope having a suitable magnifying power (e.g., 5×, 10×, 25×, 50×, 100×, 200× or greater) is used to analyze the number or amount of fibers captured by the filter, which in turn represents a degree of fibers shed from the fabric. At 430, the examination of the filter under magnification allows for a total number of fibers and/or an amount or degree of fibers per area to be determined (e.g., utilizing software associated with the microscope capable of making such calculations), and this number or amount of fibers is assigned a fiber loss or fiber shedding value based upon a grading scale as desired for a particular scenario and/or for a particular type of fabric or textile product.

Examples of amount or degree of fibers can be an actual number of fibers measured in a given area over the surface of the sample, which can be obtained visually and/or via an automated process. Alternatively, an amount of fibers can be determined based upon some other indication of amount or degree of coverage or areal density of fibers over a given area of the sample. For example, an amount or degree can be determined visually (e.g., comparing with an established chart of varying degrees of fiber density/areal coverage, and then assigning the sample to a particular category in the chart). In other examples, the amount or degree can be determined in an automated process (e.g., a measured level of opacity or light transmittance through a surface area containing collected fibers, where less light transmittance/ more opaqueness represents a greater amount or degree of fibers collected on sample). Any other suitable measurement or analysis can also be utilized to determine amount or degree of fibers collected on the filter (which indicates a degree of fibers shed from the fabric material tested).

Any suitable grading scale can be assigned to categorize number or amount of fibers captured on the filter with a degree of fiber loss/fiber shedding associated with the fabric being tested. In an example embodiment, a grading scale of 1 to 5 is assigned for a particular application (e.g., fabrics to be used to form apparel products). In this grading scale, a lower number graded for a first fabric designates more fiber loss/fiber shedding associated with the first fabric in relation to a higher number graded for a second fabric that has undergone the same fiber shedding test as the first fabric. In particular, a grading scale of 1 to 5 can correlate with the following degrees of fiber shedding:

1—extreme loss/shedding of fibers from fabric.
2—severe loss/shedding of fibers from fabric.
3—moderate loss/shedding of fibers from fabric.
4—slight loss/shedding of fibers from fabric.
5—very little to no loss/shedding of fibers from fabric.

Figure 5A:
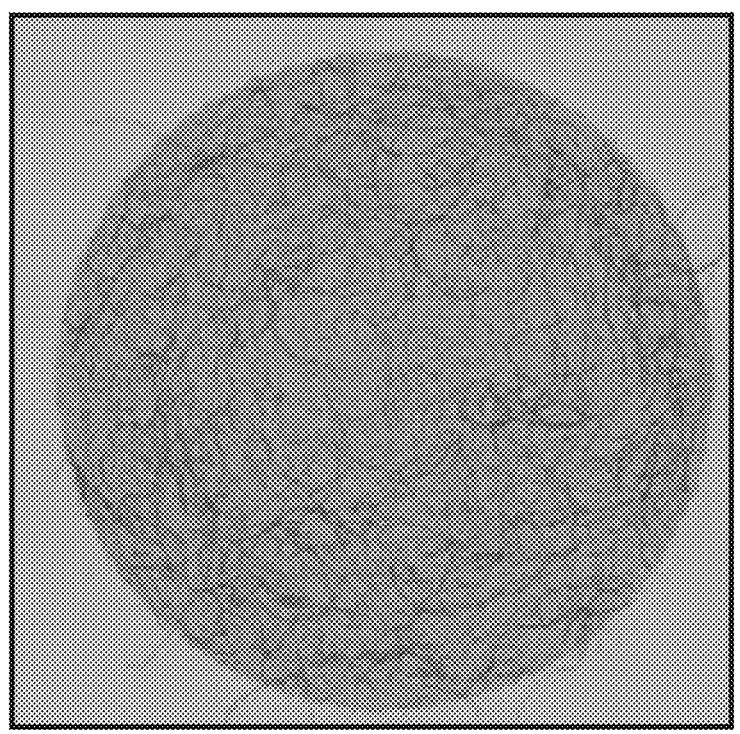
FIGS. 5A, 5B, 5C, 5D and 5E are magnified images of samples from different fabrics testing with the fiber loss/ fiber shedding test methods described herein, where each image demonstrates a grade or scale for the fabric sample based upon an amount of fiber loss or fibers shed from the fabric sample.
Figure 5B:
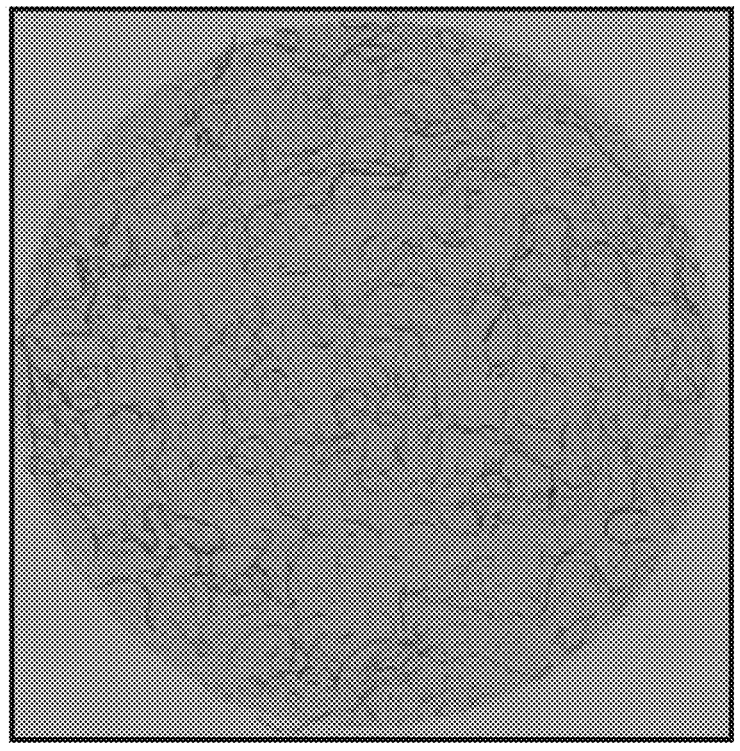
Figure 5C:
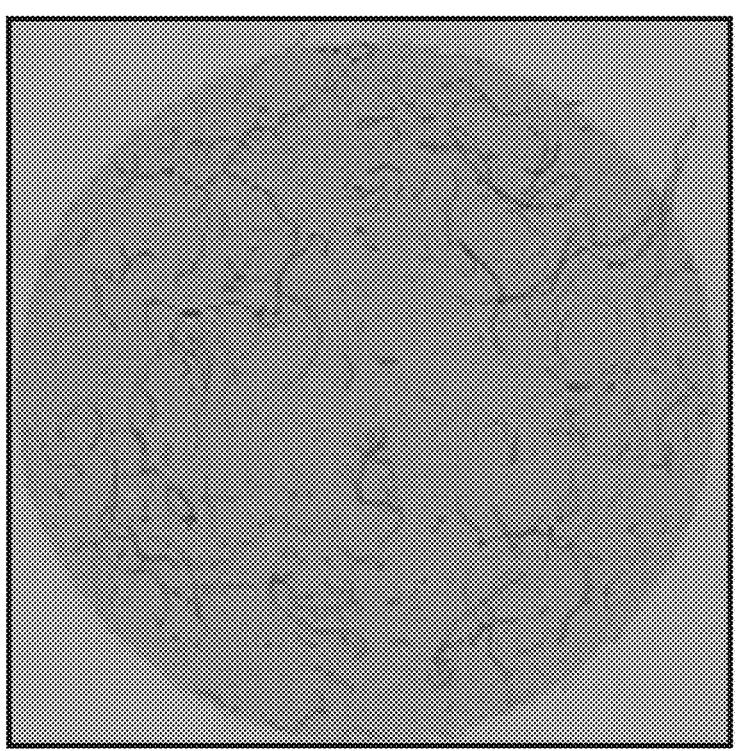
Figure 5D:
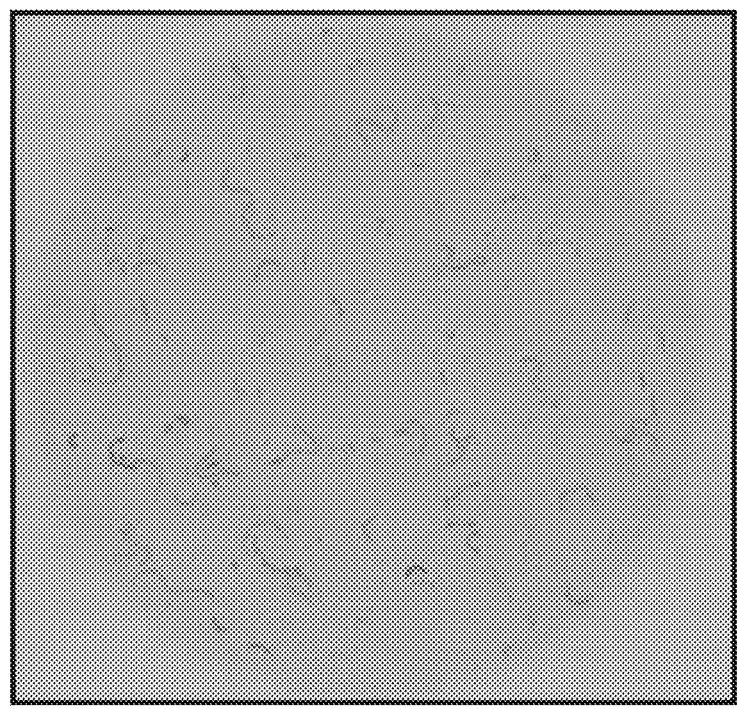
Figure 5E:
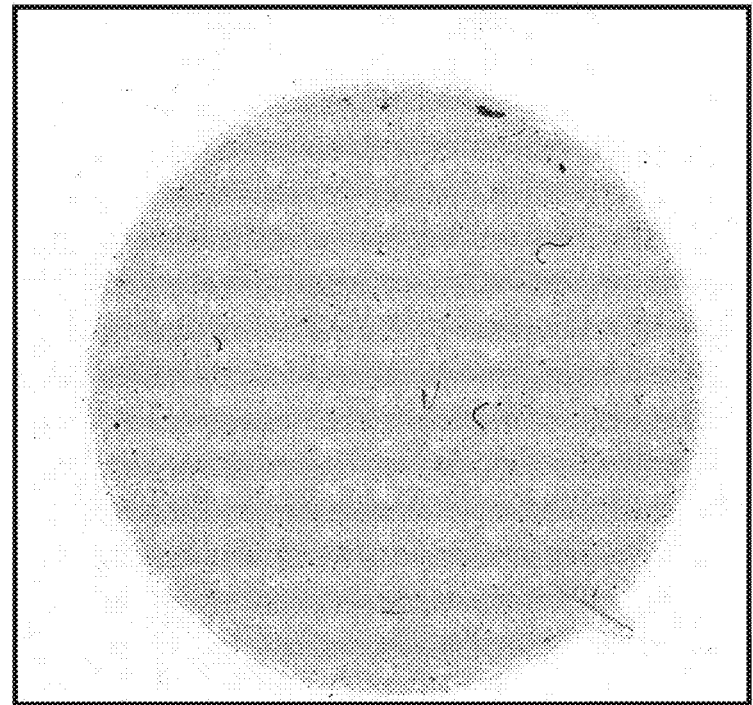

The noted grading scales 1-5 are visualized in FIGS. 5A-5E, where each figure is a magnified view of a filter that has captured fibers from a fabric sample subjected to the fiber loss/fiber shedding test methods described herein, where the test sample for each of the views is from a different fabric. In particular, FIG. 5A shows a filter in which the amount of fibers captured represents a grade of 1, FIG. 5B shows a filter in which the amount of fibers captured represents a grade of 2, FIG. 5C shows a filter in which the amount of fibers captured represents a grade of 3, FIG. 5D shows a filter in which the amount of fibers captured represents a grade of 4, and FIG. 5E shows a filter in which the amount of fibers captured represents a grade of 5. A comparison of the different views shows that the number or amount of fibers on the filter (e.g., fibers per area) decreases progressively from FIG. 5A to FIG. 5E. These views provide a visual indication of amount or concentration of fibers collected on the filter, and these visual views can be used to qualitatively assign a grading scale number to the fabric associated with the fiber covered filter obtained from the fiber shedding test. Alternatively, or in combination with the visual views and qualitative assessment, the grading scale number can be determined based upon a quantitative assessment in which the number of fibers on the filter and/or a number (e.g., an average number) of fibers counted over a select or predetermined area of the filter can be determined and used to assign a grading scale number to the fabric associated with the fiber covered filter obtained from the fiber shedding test.

While the grading scale is described herein as a 1-5 grading scale (with 5 being the best fabric or fabric with least amount of fiber shedding, and 1 being the worst fabric or fabric with most amount of fiber loss/fiber shedding), any other suitable grading scale can be assigned depending upon a particular granularity or level of distinction that is desired to be assigned for determining fiber shedding tendencies of a fabric. A finer grading scale (e.g., from 1 to 10, from 1 to 50, from 1 to 100, etc.) can also be utilized to obtain finer distinctions in fiber shedding for certain fabrics. Alternatively, a grading scale with broader classifications (e.g., scale from 1 to 3) can be developed to determine fiber shedding tendencies of fabrics to be tested. The grading scale can further utilize any selected numeric, alpha numeric, alphabetical, and/or other character designations (e.g., using a number grading scale as described herein, a letter grading scale such as A-E, a grading scale combining numbers and letters such as A1, A2, . . . B1, B2, . . . , a grading scale including colors, a grading scale comprising different shapes or different icons, etc.) to establish categories of fabrics based upon fiber loss/fiber shedding characteristics of the fabrics as determined by the methods described herein.

It is noted that the grading scale can further be defined based upon particulars of the test sample, including sample size, sample shape, type of fibers and/or fabrics that form the sample, etc. In other words, the grading scale can vary based upon a particular application, including particular type of fabric to be tested. It is important to note, however, that a selected grading scale and method for a specific sample type should be maintained constant or become a standard for all fabrics or textiles to be used for such selected grading scale.

At 440, the fiber loss/fiber shedding grade assigned a fabric based upon the test method described herein allows a manufacturer to determine the quality of a particular fabric and/or whether the fabric should be limited to certain uses. For example, a fabric having a shedding grade or shedding scale designation that indicates a very high amount or degree of fiber loss/shedding may be determined as unsuitable for use in apparel or other textile products which are subjected to a significant number of laundry washes (and thus fiber entrainment into waste water and potentially infiltration and polluting of ecosystems) over the lifespan of the textile product. Conversely, a fabric that is determined to have very low fiber loss/fiber shedding characteristics may be determined as an excellent candidate for an apparel or other textile product. A quality grading system for assigning a quality grade to a fabric material can be developed based upon determined fiber shedding characteristics of different fabric materials using the methods described herein. Types of fabrics can also be characterized and/or graded for different uses depending upon their determined fiber loss/fiber shedding characteristics. A determination of quality of fabric material based upon its fiber shedding characteristics can also be used to assign an environmental grade or value to the fabric (e.g., a high fiber shedding material correlates with a low or worse environmental grade, while a lower fiber shedding material correlates with a higher or better environmental grade).

Thus, the methods described herein facilitate identifying fabrics and/or components of fabrics (e.g., types of fibers forming the fabrics, types of fabric forming techniques, etc.) that shed or lose fewer fibers and thus are more environmentally friendly and potentially less prone to wear and tear (due to maintaining integrity of the fiber count/fiber structure within the fabric) over the lifespan of the fabric.

While the invention has been described in detail and with reference to specific embodiments thereof, it will be apparent to one skilled in the art that various changes and modifications can be made therein without departing from the spirit and scope thereof.

It is thus intended that the present invention covers the modifications and variations of this invention provided they come within the scope of the appended claims and their equivalents. It is to be understood that terms such as "top", "bottom", "front", "rear", "side", "height", "length", "width", "upper", "lower", "interior", "exterior", and the like as may be used herein, merely describe points of reference and do not limit the present invention to any particular orientation or configuration.

What is claimed:

1. A method of determining an amount of fiber loss from a fabric material after washing of the fabric material, the method comprising:

providing a sample of the fabric material within a container, the sample having a shape defined by peripheral edge portions of the sample, wherein the providing the sample within the container comprises pinching the peripheral edge portions of the sample between facing surfaces within the container;

adding water into the container to facilitate contact of the water with a surface of the sample that faces the water while preventing the water from contacting the peripheral edge portions of the sample;

agitating the water within the container for a predetermined period of time so as to cause fibers to be released from the fabric material and entrained in the water;

after agitating, transferring the water with entrained fibers from the container into a fiber collection system to obtain captured fibers; and analyzing the captured fibers to determine a degree of fibers shed from the fabric material.

2. The method of claim 1, further comprising:

cutting the sample from the fabric material in a shape that corresponds with a cross-sectional shape of the container.

3. The method of claim 1, wherein the agitating of the water within the container comprises:

inserting a stir bar into the container including the sample; and facilitating a rotation of the stir bar within the container filled with water for the predetermined time period.

4. The method of claim 1, wherein the container comprises a vessel with an open end and a lid that is securable to the open end of the vessel, the sample is provided between the vessel and the lid, and the lid is secured to the vessel such that the edges of the sample are pinched and covered by the facing surfaces of a container edge at the open end of the container and a surface of the lid that faces the container edge.

5. The method of claim 1, wherein the fiber collection system comprises a filtration system including a filter and a filtration vessel, and the transferring the water with entrained fibers from the container into the fiber collection system to obtain captured fibers comprises:

directing the water with entrained fibers to the filtration system and onto the filter so as to separate the water from the entrained fibers in the water by passing the water through the filter and into the filtration vessel while the fibers are collected on the filter.

6. The method of claim 5, wherein the analyzing the captured fibers comprises:

analyzing the filter including collected fibers under one or more magnified views to determine an amount of collected fibers on the filter.

7. The method of claim 5, wherein the filter has a pore size of at least 0.5 micrometers.

8. The method of claim 5, wherein the filter comprises a mixed cellulose ester (MCE) membrane filter material.

9. The method of claim 5, wherein the filtration system further comprises a funnel, the filtration vessel comprises a flask including an open end that is in fluid communication with the funnel, the filter is disposed between the funnel and the open end of the flask, and the method further comprises:

applying a vacuum to an outlet port of the flask to draw water from the funnel, through the filter and into the flask.

10. The method of claim 5, wherein the analyzing the captured fibers comprises analyzing a magnified view of the filter to determine an amount of fibers collected on the filter and disposed along a predetermined area of a surface of the filter.

11. The method of claim 10, further comprising:

assigning a value based upon the determined amount of fibers collected on the filter; and correlating the assigned value to the degree of fibers shed from the fabric material.

12. The method of claim 1, wherein at least some of the fibers released from the fabric material have cross-sectional dimensions of no greater than 10 micrometers.

13. The method of claim 1, further comprising:

assigning an indicator of fiber loss to the fabric material based upon the determined degree of fibers shed from the fabric material.

14. The method of claim 13, wherein the determined degree of fibers shed from the fabric material comprises a measured number of fibers shed from the fabric material.

15. The method of claim 1, further comprising:

determining a quality of the fabric material based upon the determined degree of fibers shed from the fabric material.

16. The method of claim 15, wherein the determining the quality of the fabric material further comprises:

assigning a quality grade for the fabric material based upon the determined degree of fibers shed from the fabric material.

17. A method of determining an amount of fiber loss from a fabric material after washing of the fabric material, the method comprising:

providing a sample of the fabric material within a container, the sample having a shape defined by peripheral edge portions of the sample;

adding water into the container to facilitate contact of the water with a surface of the sample that faces the water while preventing the water from contacting the peripheral edge portions of the sample;

agitating the water within the container for a predetermined period of time so as to cause fibers to be released from the fabric material and entrained in the water;

after agitating, transferring the water with entrained fibers from the container into a fiber collection system to obtain captured fibers, wherein the captured fibers are collected along a surface of a filter; and analyzing the captured fibers to determine a degree of fibers shed from the fabric material, wherein the analyzing comprises determining an amount of fibers per area along the surface of the filter based upon a count of fibers.

18. A method of determining an amount of fiber loss from a fabric material after washing of the fabric material, the method comprising:

securing a sample of the fabric material at a secured location within a container, the sample having a shape defined by peripheral edge portions of the sample;

adding water into the container to facilitate contact of the water with a surface of the sample that faces the water while preventing the water from contacting the peripheral edge portions of the sample;

agitating the water within the container for a predetermined period of time so as to cause fibers to be released from the fabric material and entrained in the water, wherein the fabric material remains secured and is prevented from moving from the secured location within the container during the agitating;

after agitating, transferring the water with entrained fibers from the container into a fiber collection system to obtain captured fibers; and analyzing the captured fibers to determine a degree of fibers shed from the fabric material.

\* \* \* \* \*